United States Patent [19]

Fikentscher et al.

[11] Patent Number: 4,614,613

[45] Date of Patent: Sep. 30, 1986

[54] PREPARATION OF β-N-AZIRIDINOPROPIONATES

[75] Inventors: Rolf Fikentscher; Siegfried Schneider; Erhard Klahr, all of Ludwigshafen; Friedrich Reinert, Wachenheim; Günter Eckert, Limburgerhof; Adolf Stuebinger, Frankenthal, all of Fed. Rep. of Germany

[73] Assignee: BASF Aktiengesellschaft, Rheinland, Fed. Rep. of Germany

[21] Appl. No.: 628,773

[22] Filed: Jul. 9, 1984

[30] Foreign Application Priority Data

Jul. 9, 1983 [DE] Fed. Rep. of Germany ....... 3324917

[51] Int. Cl.$^4$ ............................................. C07D 203/08
[52] U.S. Cl. ........................................ 548/964; 548/968
[58] Field of Search ........................ 260/239 A, 239 E

[56] References Cited

U.S. PATENT DOCUMENTS

| 2,789,968 | 4/1957 | Reynolds et al. | 260/463 |
| 3,853,960 | 12/1974 | Crowther | 260/482 B |
| 4,025,503 | 5/1977 | Miksovsky et al. | 260/239 E |
| 4,052,384 | 10/1977 | Dockner et al. | 260/239 E |
| 4,252,737 | 2/1981 | Krimm et al. | 260/463 |
| 4,263,446 | 4/1981 | Wheeler et al. | 560/75 |
| 4,267,303 | 5/1981 | König et al. | 260/463 |
| 4,281,101 | 7/1981 | Schreckenberg et al. | 260/463 |

FOREIGN PATENT DOCUMENTS 1544210 9/1968 France .
813798 5/1959 United Kingdom .

OTHER PUBLICATIONS

Thieme et al., *Chemical Abstracts*, vol. 81: 106342a, 1974.
Yamazaki et al., *Chemical Abstracts*, vol. 91: 92272v, 1979.
Mitsui Toatsu Chemicals, Inc., *Chemical Abstracts*, vol. 96: 68355g, 1982.
Interscience Publishers, 1963, vol. I, p. 314, G. A. Olah, "Friedel–Crafts and Related Reactions".
Industrieverlag von Hernhaussen K.-G., 1962, vol. 64, pp. 110–113, "Fette, Seifen, Anstrichmittel".

*Primary Examiner*—Donald G. Daus
*Assistant Examiner*—Stephen M. Kapner
*Attorney, Agent, or Firm*—Oblon, Fisher, Spivak, McClelland & Maier

[57] ABSTRACT

β-N-aziridinopropionates of relatively high boiling alcohols or polyalcohols are prepared by transesterifying a β-N-aziridinopropionate of a lower alcohol of 1 to 4 carbon atoms with a relatively high boiling alcohol or polyalcohol by a process in which the transesterification is carried out in the presence of, as a transesterification catalyst, a titanium(IV) or tin(IV) compound which is soluble in an organic medium.

7 Claims, No Drawings

PREPARATION OF β-N-AZIRIDINOPROPIONATES

The present invention relates to a process for the preparation of β-N-aziridinopropionates of relatively high boiling alcohols and polyalcohols by transesterification of a β-N-aziridinopropionate of a lower alcohol of 1 to 4 carbon atoms in the presence of, as a transesterification catalyst, a titanium(IV) or tin(IV) compound which is soluble in organic solvents.

β-aziridinopropionates of diols or polyols are useful crosslinking agents for alkylatable OH-containing, NH-containing and SH-containing polymers and substrates. They are therefore employed for reactions with polymeric resins, aqueous dispersions or aqueous polymer solutions in the coating and finishing sector, or are used as treatment agents for sheet-like structures.

The synthesis routes described for the preparation of such aziridinopropionates all have certain disadvantages:

1. The addition reaction of ethyleneimine with a polyfunctional acrylate in accordance with the equation

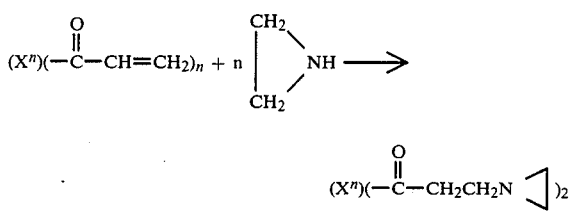

where X is derived from a diol or polyol, for example trimethylolpropane, pentaerythritol, sorbitol and the like, which may be oxyalkylated with ethylene oxide (EO) and/or propylene oxide (PO), or from a polyether obtained from ethylene oxide and/or propylene oxide and/or butylene oxide and/or tetrahydrofuran.

This conventional route (U.S. Pat. No. 2,569,200, German Laid-Open Application No. DOS 1,754,810, and R. Hüttel, Fette Seifen Anstrichmittel 64 (1962) 110 et seq.) has, for example, the following disadvantages:

The starting material, ie. the polyfunctional acrylate, is often insufficiently pure since, in spite of the presence of stabilizers during the preparation of the acrylate, undesirable polymerization of the double bond may still take place. Industrial-scale purification of the polyfunctional acrylates by distillation is not possible.

The acid which is used for the esterification of the acrylic acid, and which, because of polymerization of aziridine, is absolutely necessary before the further reaction with ethyleneimine, is difficult to separate off or neutralize. Traces of acid or salts frequently cause the aziridine-containing end products to have a short shelf life.

When the reaction is carried out using equimolar amounts, the addition of ethyleneimine at the double bond of the acrylate takes place very slowly and non-quantitatively toward the end of the reaction. When excess ethyleneimine is used, quantitative removal of the monomer presents problems.

A side reaction which occurs is the amidation of the resulting ester by ethyleneimine:

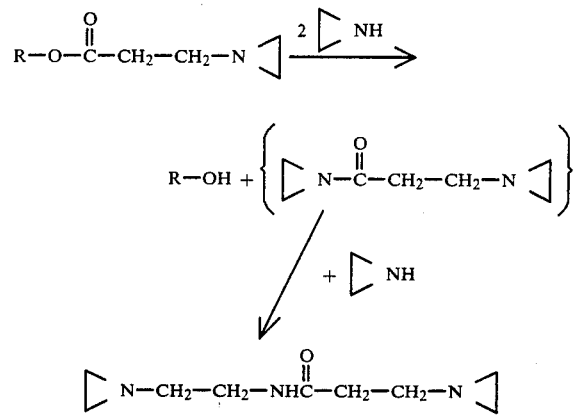

2. The transesterification of methyl β-aziridinopropionate with one of the abovementioned polyols in the presence of an alkali metal alcoholate, a tertiary amine or a metal oxide, such as CaO or $TiO_2$, as described in French Pat. No. 1,544,210 or German Laid-Open Applications Nos. DOS 2,334,656 or DOS 2,521,859:

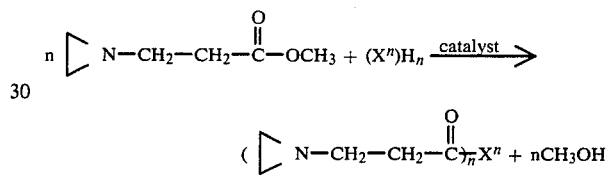

Depending on the catalyst, the reaction temperature and the reaction medium, this transesterification reaction is accompanied by side reactions, such as elimination of ethyleneimine from the β-aziridinopropionate group and partial polymerization of the threemembered ring or of the double bonds formed as a result of amine elimination.

Both side reactions reduce the reactivity of the aziridine crosslinking agent. Although some of the ethyleneimine eliminated is removed from the end product during the transesterification, the end product still contains a residual amount as a relatively toxic monomer.

When catalysts, such as CaO or $TiO_2$, which are sparingly soluble or insoluble in the reaction medium are used, the catalyst has to be separated off by filtration in order to avoid difficulties in subsequent processing. The transesterification time is longer, in the presence of the said metal oxides than when the claimed catalysts are used.

We have found that the elimination of ethyleneimine from the β-aziridinopropionates and the polymerization of aziridine during the transesterification can be substantially avoided if titanium(IV) or tin(IV) compounds which are soluble in organic media are used as transesterification catalysts.

The present invention relates to a process for the preparation of β-N-aziridinopropionates of relatively high boiling alcohols and polyalcohols by transesterification of a β-N-aziridinopropionate of a lower alcohol of 1 to 4 carbon atoms with a relatively high boiling alcohol or polyalcohol, wherein the transesterification is carried out in the presence of, as a transesterification catalyst, a titanium(IV) or tin(IV) compound which is soluble in an organic medium.

Examples of lower β-aziridinopropionates are, in particular, the methyl, ethyl and butyl esters, the methyl ester being particularly preferred.

Relatively high boiling alcohols and polyalcohols are those having boiling points above 120° C. Particularly suitable alcohols are primary and secondary aliphatic alcohols, such as decanol, lauryl alcohol or stearyl alcohol, while particularly suitable polyols are ethylene glycol, propylene glycol, glycerol, pentaerythritol, sorbitol and trimethylolpropane and their oxyalkylation products containing in each case from 1 to 50, preferably from 3 to 20, moles of ethylene oxide and/or propylene oxide and/or butylene oxide, and polytetrahydrofurans having molecular weights of from 800 to 3000 and their copolymers with epoxides. The stated polyols and their oxyalkylation products containing from 3 to 20 moles of alkylene oxide and polytetrahydrofuran having a mean molecular weight of 800–3000 are particularly preferred.

Transesterification catalysts used according to the invention are compounds of tetravalent titanium, preferably tetraalkyl titanates where alkyl is of 1 to 10 carbon atoms, and compounds of tetravalent tin of the general formula $R_mSnX_{4-m}$, where R is a saturated organic alkyl radical of 1 to 10 carbon atoms, X is oxygen or is an alkyl radical or an acyl radical of an organic acid of 1 to 18 carbon atoms, these radicals being bonded via an oxygen atom, in particular alkyl of 2 to 8 carbon atoms or an acyl radical of an organic mono- or dicarboxylic acid of 2 to 8 carbon atoms and m is an integer from 1 to 3, the said compounds being soluble in organic media.

Specific examples are tetramethyl titanate, tetraethyl titanate, tetrabutyl titanate, tetraisobutyl titanate and tetra-2-ethylhexyltitanate, as well as dibutoxydibutyltin, dimethoxydimethyltin, dibutyltin dilaurate, dioctyltin dipalmitate, dibutyltin maleate and bistributyltin oxide.

Tetra-$C_1$-$C_8$ alkyl titanates, dibutyltin oxide, dibutyltin dilaurate, dibutoxydibutyltin and bistributyltin oxide are preferred.

The actual transesterification is advantageously carried out at from 80° to 180° C., preferably from 100° to 160° C., under atmospheric pressure or, if required, under reduced pressure as low as 10 mbar. In an advantageous embodiment, a liquid saturated aliphatic hydrocarbon of 6 to 10 carbon atoms, in particular octane, or nitrogen is used as an entraining agent or stripping agent to remove the lower alcohol from the equilibrium.

Compared with the metal oxide catalysts described, ie. MgO, CaO or $TiO_2$, substantially smaller amounts of the catalysts used according to the invention accelerate the transesterification reaction to a greater extent, so that the reaction time is reduced by more than a half.

The titanates and stannates dissolve in the reaction mixture to give a homogeneous solution and, in contrast to the metal oxides, do not have to be separated off by filtration when the transesterification is complete.

Since aziridine compounds polymerize readily in the presence of acids or Lewis acids, the fact that Ti (IV) compounds, which are known to be Lewis acids, could be used for the transesterification of aziridine-containing compounds (cf. G.A. Olah "Friedel Crafts and related reactions", Interscience Publ. 1963, Vol. I, page 314, and British Pat. No. 813,798) is surprising and could not be foreseen by a skilled worker.

The novel catalysts are used in amounts of from 0.01 to 0.3% by weight, based on the two reactants. The transesterification is complete in the course of from 1.5 to 4 hours, the end being detected from the amount of lower alcohol distilled off (as a rule, >97% of theory).

If methyl β-aziridinopropionate is used for the transesterification, it is advantageous to use a $C_6$-$C_{10}$-paraffin as an azeotropic entraining agent for removing the methanol.

In contrast to the alkali metal alcoholates, the titanium and tin compounds used according to the invention do not catalyze the β-elimination of ethyleneimine from the β-N-aziridinopropionates. Because the transesterification temperature can be kept relatively low, and the duration of the transesterification is greatly reduced, virtually no polymerization of the three-membered ring takes place in the transesterification mixture.

The efficiency of various transesterification catalysts is demonstrated in the synthesis of a bisaziridinopropionate of a polytetrahydrofuran (molecular weight 2000) by the transesterification of methyl aziridinopropionate with polytetrahydrofuran-2000 at from 110° to 140° C. in the presence of octane. The improvement in the conversion obtained using the titanium and tin catalysts compared with that obtained using the conventional catalysts (alkali metal alcoholates, CaO and $TiO_2$) is evident from the increased aziridine content of the diester (96–98% of theory compared with 88–93% of theory), from the smaller amount of ethyleneimine monomer distilled off and from the color number of the end products. The results are summarized in the table below.

TABLE 1

| | Catalyst | Amount of catalyst in % by weight, based on polytetrahydrofuran and aziridinopropionate | Reaction time until isolation of 97% of the methanol (hours) | Aziridine content in the end product (% of theory) | Ethyleneimine in the distillate, in % by weight, based on total aziridine used | Iodine color number |
|---|---|---|---|---|---|---|
| | $NaOCH_3$ | 0.02 | 8 | 88 | 5.8 | 8 |
| | $NaOCH_3$ | 0.10 | 4.5 | 93 | 2.7 | 6 |
| Comparison | $NaOCH_3$ | 0.24 | 2 | 93 | 5.4 | 10 |
| | K tert.-butylate | 0.24 | 2 | 91 | 5.2 | 5 |
| | CaO | 1.76 | 6 | 90 | 0.06 | 1 |
| | $TiO_2$ | 0.88 | 7.5 | 89 | 0.06 | 1 |
| | Tetrabutyl titanate | 0.015 | 2 | 98 | 0.04 | 1 |
| | Tetrabutyl titanate | 0.06 | 1.75 | 99 | 0.02 | 1 |
| | Triethyl titanate | 0.03 | 2.5 | 96 | 0.07 | 1 |
| | Dibutyltin dilaurate | 0.1 | 2.45 | 98 | 0.014 | 1 |
| | Dibutyltin oxide | 0.1 | 3 | 96 | 0.02 | 1 |

The polyfunctional aziridinopropionates can advantageously be used as crosslinking agents, for example for finishing wool and for the crosslinking of water-soluble polymers or of dispersions in the manufacture of paper, textiles and leather. The compounds which contain only one aziridine ring are reactive plasticizers and handle finishing agents.

COMPARATIVE EXPERIMENTS I-IV

I. 264 g of octane and 161 g (1.24 moles) of methyl β-N-aziridinopropionate containing 15 ppm by weight of ethyleneimine were added to 1200 g (0.615 mole) of dried polytetrahydrofuran-2000 having an OH number of 57.4 mg of KOH/g. 3.3 g (0.24% by weight, based on polytetrahydrofuran and aziridinopropionate) of sodium methylate were added, after which the reaction solution was heated (bath temperature 150°-160° C.) and the solvent and the methanol were distilled off, the octane being recycled. The temperature of the reaction mixture was from 122° to 140° C., and 38.5 g (1.2 moles) of methanol were separated off in the course of 2 hours. The solvent was then distilled off under reduced pressure from a water pump and at a bath temperature up to 100° C., and two downstream cold traps cooled by means of dry ice were provided to ensure that neither solvent nor ethyleneimine was lost. The residue amounted to 1,320 g. Gas chromatographic determination showed that the distillates contained the following amounts of ethyleneimine:

| | | |
|---|---|---|
| Ethyleneimine in the octane layer | 17 millimoles | 67 millimoles |
| Ethyleneimine in the methanol layer | 50 millimoles | |

The aziridine content of the product was 0.86 millimole/g (theory: 0.93 millimole/g). A 50% strength solution of the aziridino ester in isopropanol had an iodine color number of 10.

The amounts and types of catalysts shown below were used to carry out transesterification reactions by a method similar to that described above.

ture was 135°-140° C. The methanol formed distilled over azeotropically with the octane and separated from the latter after cooling. As long as 6 hours were required to distill off 39 g (99% of theory) of methanol azeotropically from the reaction mixture.

The reaction mixture was freed from solvent under reduced pressure from a water pump and at a bath temperature of 100° C., and was then freed from excess calcium oxide over a suction filter at about 60° C. The yield was 1300 g. In order to obtain a clear filtrate, filtration had to be carried out using about 20 g of a filter aid and a very fine-pored filter plate.

The distillates were found to contain 0.74 millimole of ethyleneimine monomer (0.64 millimole in the methanol fraction and 0.10 millimole in the octane phase). The product contained 0.83 meq/g (theory: 0.92 meg/g) of aziridine and 1.5 ppm of ethyleneimine.

VI. When the reaction was carried out under similar conditions but with 12.2 g of titanium(IV) oxide instead of the calcium oxide, 7.5 hours were required to separate off 39 g of methanol in the transesterification.

The distillates were found to contain 0.70 millimole of ethyleneimine. To enable the catalyst to be separated off quantitatively by centrifuging, the reaction mixture had to be very greatly diluted. A 50% strength solution of the end product in isopropanol had an aziridine content of 0.41 meq/g (theory: 0.46 meq/g).

EXAMPLES 1-3

(according to the invention)

1. 264 g of octane and 162 g (1.25 moles) of methyl β-N-aziridinopropionate were added, in the absence of water, to 1200 g (0.59 mole) of polytetrahydrofuran-2000 having an OH number of 55.1 mg of KOH/g. The mixture was heated to 60° C. and stirred thoroughly, and 0.2 g (0.015% by weight, based on polytetrahydrofuran and aziridino ester) of tetrabutyl orthotitanate was added. 37 g of methanol were distilled off azeotropically together with octane in the course of 2 hours at a bath temperature of 155°-160° C., the bottom temperature being from 126° to 140° C.

Excess solvent was then distilled off from the esterifi-

TABLE 2

| Comparison | Type of catalyst | Amount in g | Reaction time (hours) | Amount of methanol separated off g | Amount of ethyleneimine in the distillate mmol | Amount of ethyleneimine in the product ppm | Aziridine content of the product mmol/g | Iodine color number of the end product |
|---|---|---|---|---|---|---|---|---|
| II | Sodium methylate | 0.10 | 4.5 | 38.0 | 34 | 3.8 | 0.86 | 6 |
| III | Sodium methylate | 0.02 | >8 | 36.0 | 72 | — | 0.82 | 8 |
| IV | Potassium tert. butylate | 0.24 | 2 | 39.0 | 65 | 4.6 | 0.85 | 5 |

COMPARATIVE EXPERIMENTS V and VI

V. 24 g (1.76 parts per 100 parts of polytetrahydrofuran and aziridino ester) of calcium oxide which had been freshly calcined for 4 hours at 700° C. were added to 1200 g (0.61 mole) of polytetrahydrofuran-2000 having a hydroxyl number of 56.8 mg of KOH per g, 264 g of octane and 160 g (1.24 moles) of methyl β-N-aziridinopropionate containing 15 ppm of ethyleneimine. The thoroughly stirred suspension was distilled at a bath temperature of 160° C. During the distillation, the bottom temperature in the transesterification mixcation mixture under reduced pressure (16 mbar) from a water pump and at a bath temperature of 100° C. The distillates contained 0.47 millimole of ethyleneimine monomer (0.42 millimole in the methanol layer and 0.05 millimole in the octane layer). 0.24 vol ppm of ethyleneimine monomer were detectable in the 100% pure substance. The end product contained 0.88 millimoles/g (theory: 0.90 millimole/g) of aziridine and the iodine color number of a 50% strength solution in isopropanol was 1.

2. When the transesterification was carried out in the presence of 0.81 g (0.061 parts by weight per 100 parts by weight of polytetrahydrofuran and aziridino ester) of tetrabutyl titanate, otherwise using the same starting materials and amounts, the reaction was complete after 1¾ hours, 37 g of methanol having been distilled off. The distilled solutions contained 0.19 millimole (0.16+0.03 millimole) of ethyleneimine monomer, and the end product contained 0.895 millimoles/g (theory: 0.90 millimoles/g) of aziridine.

3. When 0.03 parts by weight of tetraethyl orthotitanate were used per 100 parts by weight of polytetrahydrofuran and methyl aziridinopropionate, similar results were obtained in a transesterification time of 2½ hours: 0.89 millimole of ethyleneimine monomer were distilled off with the solvents, and the aziridine content of the end product was 0.87 millimole/g.

EXAMPLES 4 and 5

4. A mixture of 1200 g of polytetrahydrofuran having an OH number of 55.1 mg of KOH/g, 162 g of methyl β-N-aziridinopropionate containing ≦10 ppm of ethyleneimine monomer, and 264 g of octane was heated to 50° C., 1.4 g of dibutyltin oxide were added, and the methanol formed during the transesterification was then distilled off azeotropically with the octane, at a bath temperature of 155° C. The reaction was complete after 3 hours. When the solvent had been distilled off under reduced pressure from a water pump, gas chromatographic determination showed that the distillates contained 0.20 millimole of ethyleneimine monomer. The aziridine content of the clear colorless end product was 0.87 millimole/g (96% of theory).

5. A similar experiment in which 1.4 g of dibutyltin dilaurate were used as the catalyst gave, after transesterification for 2¾ hours, a polytetrahydrofuran-2000 bis-aziridinopropionate having an aziridine content of 0.88 millimoles/g. Only 0.17 millimole of ethyleneimine monomer were detectable as a cleavage product in the distillates. The reaction product was a clear colorless melt which crystallized slowly at 48° C.

EXAMPLE 6

1200 g of anhydrous polytetrahydrofuran having an OH number of 55.1 mg of KOH/g and a molecular weight of 2033 were melted, and 162 g of methyl β-N-aziridinopropionate containing <10 ppm of ethyleneimine monomer were added at 50° C., 0.2 g of tetrabutyl orthotitanate was introduced and the mixture was then heated at 140°–155° C. (bath temperature). The methanol formed was distilled off over a short column, under a gentle stream of nitrogen. After a reaction time of 2½ hours at a bottom temperature of 136°–152° C. the transesterification was complete. The reaction mixture was freed from volatile constituents under reduced pressure from a water pump, and the amount of eliminated ethyleneimine monomer in the distillates from the receiver and the cold traps was determined. This was 1.3 millimoles corresponding to 0.10% of the amount of aziridine used. The colorless transesterification product, which formed a clear melt, contained 0.87 millimole/g (ie. 97% of theory) of aziridine.

EXAMPLE 7

The bisaziridinopropionate of polytetrahydrofuran-1000 was prepared from 588 g of polytetrahydrofuran-1000 having an OH number of 110.5, 165 g of methyl aziridinopropionate and 0.14 g of tetrabutyl orthotitanate in the course of 3.5 hours, using a procedure similar to that described in Example 6. The amount of ethyleneimine monomer distilled off was 1.5 millimoles, corresponding to 0.12% of the amount of aziridine used. The ester obtained contained 1.56 millimoles/g (theory: 1.66 millimoles/g) of aziridine. The clear 50% strength solution of the ester in isopropanol had a viscosity of 40 mPa.s (20° C.) and a refractive index $n_D^{20}$ of 1.4258.

EXAMPLE 8

252 g of oxypropylated sorbitol having an OH content of 3.98 millimoles/g, 156 g of methyl β-N-aziridinopropionate, 100 g of octane and 10 g of methanol were dried for 1 hour at a bottom temperature of 132° C., methanol and traces of water being separated off. 0.4 g of tetrabutyl titanate was then added, and methanol was distilled off azeotropically at bottom temperatures of 126°–142° C. After 4½ hours, 37 g of methanol had been separated off. The mixture was freed from solvent under reduced pressure from a water pump and at a bath temperature of up to 100° C. The slightly colored residue (352 g) contained 2.7 millimoles/g (98.4% of theory) of aziridine and had a refractive index $n_D^{20}$ of 1.4630. The product is an effective crosslinking agent for binders for textile printing.

EXAMPLE 9

302 g of a pentaerythritol oxyalkylated with 8 moles of butylene oxide and 8 moles of propylene oxide, 100 g of octane and 10 g of methanol were dried by separating off methanol and water, and 0.5 g of tetrabutyl titanate and 133 g of methyl β-N-aziridinopropionate were then added. Transesterification was then carried out for 4.5 hours at a bottom temperature of 123°–146° C., a methanol/octane azeotrope being distilled off. The mixture was then freed from the solvent under reduced pressure from a water pump and at a bath temperature up to 100° C. The residue (408 g) was a pale brown viscous liquid and had an aziridine content of 2.55 millimoles/g, an amine number of 2.57 millimoles/g and a refractive index $n_D^{20}$ of 1.4619. The product is useful as a crosslinking agent in pigment pastes for textile printing.

EXAMPLE 10

451 g of a pentaerythritol oxyalkylated with ethylene oxide and having an OH content of 6.64 millimoles/g, 200 g of octane and 20 g of methanol were dried by distilling off methanol/water azeotropically for 1 hour, the octane being recycled. 0.9 g of tetrabutyl titanate and 387 g of methyl β-N-aziridinopropionate were then added, and transesterification was carried out at a bottom temperature of 127°–138° C. in the course of 3 hours, methanol being separated off azeotropically and the octane being recycled. The volatile constituents were distilled off under reduced pressure from a water pump to give a slightly colored viscous residue which dissolved in water to give a clear solution and had an amine number of 4.01 millimoles/g and an aziridine content of 3.98 millimoles/g. The ethyleneimine content of the sample was less than 10 ppm (limit of detection). The product produced good effects when used as a crosslinking agent for binder dispersions in the coating of leather.

EXAMPLE 11

452 g (3.5 moles) of methyl aziridinopropionate were added to a dried suspension of 136 g (1 mole) of pentaerythritol in 150 g of octane, and 0.5 g of tetrabutyl titanate was added. By means of distillation at a bottom temperature of 120°–135° C., 96 g of methanol were separated off azeotropically in the course of 3 hours. The solvent and excess methyl aziridinopropionate were then distilled off under reduced pressure from a water pump. The slightly colored viscous residue had an aziridine N content of 6.8 meq/g (theoretical value for pentaerythritol triaziridinopropionate: 7.0 meq/g) and contained 6.9 meq/g of basic nitrogen. The product is a good water-soluble cross-linking agent for carboxyl-containing polymers.

EXAMPLES 12 and 13

80 g of butanediol and 150 g of octane were added to 284 g of methyl aziridinopropionate, 0.8 g of dibutoxydibutyltin was introduced and methanol was then separated off azeotropically, 2 moles of methanol being separated off after 2.5 hours. The solvent was distilled off under reduced pressure from a water pump, after which the butanediol bisaziridinopropionate was distilled off under 0.5 mbar and at 169°–173° C. The yield was 97% of theory and the aziridine N content was 9.75 meq/g (theoretical value 9.75). The compound can be used as a crosslinking agent for polymers containing acid or mercapto groups.

Similar results were obtained when 0.7 g of bistributyltin oxide was used as the transesterification catalyst. After a reaction time of 2.5 hours, the yield was 96% of theory and the content of aziridine groups was 9.80 meq/g.

EXAMPLES 14 and 15

A mixture consisting of 170 g of stearyl alcohol, 129 g of methyl aziridinopropionate, 100 g of octane and 0.1 g of tetrabutyl titanate was subjected to azeotropic distillation to free it from the methanol formed, and the octane was recycled. After distillation for 1.5 hours, 1 mole of methanol had been separated off. The solvent was distilled off under reduced pressure from a water pump, and octadecyl aziridinopropionate remained as a residue which solidified at about 42° C. The yield was 99% of theory, the content of aziridine groups was 2.53 meq/g (theory: 2.72 meq/g), and the content of basic nitrogen in the product was 2.68 meq/g. Emulsions of this product can be used as reactive plasticizers for textiles.

Decyl β-aziridinopropionate was obtained from methyl aziridinopropionate and decyl alcohol by means of a similar reaction.

We claim:

1. A process for the preparation of a β-N-aziridinopropionate of a relative high boiling alcohol or polyalcohol, which comprises:

transesterifying a β-N-aziridinopropionate of a lower alcohol of 1 to 4 carbon atoms with a relatively high boiling alcohol or polyalcohol in the presence of from 0.01–0.3% by weight, based on the reactants, of a titanium (IV) or tin (IV) compound, which is soluble in an organic medium, at a temperature of 80° to 180° C.; and removing the lower alcohol which is liberated by the transesterification reaction by entraining the lower alcohol from the reaction medium with a liquid saturated hydrocarbon or by stripping the alcohol from the medium with nitrogen gas.

2. The process of claim 1, wherein said liquid hydrocarbon is of six to ten carbon atoms.

3. The process of claim 2, wherein said hydrocarbon is octane.

4. The process of claim 1, wherein said catalyst is tetramethyl titanate, tetraethyl titanate, tetrabutyl titanate, tetraisobutyl titanate, tetra-2-ethylhexyl titanate, dibutoxydibutyltin, dimethoxydimethyltin, dibutyltin dilaurate, dioctyltin dipalmitate, dibutyltin maleate or bistributyltin oxide.

5. The process of claim 1, wherein said catalyst is a tetra-$C_1$–$C_8$-alkyl titanate, dibutyltin oxide, dibutyltin dilaurate dibutoxydibutyltin or bistributyltin oxide.

6. The process of claim 1, wherein said alcohol is decanol, lauryl alcohol or stearyl alcohol.

7. The process of claim 1, wherein said polyalcohol is ethylene glycol, propylene glycol, glycerol, pentaerythritol, sorbitol, trimethylolpropane, their oxyalkylation products containing from 1 to 50 moles of ethylene oxide, propylene oxide and/or butylene oxide or polytetrahydrofuran of a molecular weight of 800 to 3000.

* * * * *